(12) United States Patent
Ellis

(10) Patent No.: US 6,561,188 B1
(45) Date of Patent: May 13, 2003

(54) NASAL BREATHING APPARATUS AND METHODS

(76) Inventor: Alan D. Ellis, 65 Jami St., Livermore, CA (US) 94518

( * ) Notice: Subject to any disclaimer, the term of this patent is extended or adjusted under 35 U.S.C. 154(b) by 0 days.

(21) Appl. No.: 09/643,022

(22) Filed: Aug. 21, 2000

(51) Int. Cl.[7] ............................ A62B 7/10; A61M 16/00
(52) U.S. Cl. ............................ 128/206.11; 128/207.18; 128/203.22; 128/204.12; 128/204.13
(58) Field of Search .................. 128/207.18, 204.18, 128/203.22, 200.26, 848–867, 206.11, 204.12, 204.13

(56) References Cited

U.S. PATENT DOCUMENTS

| | | | | |
|---|---|---|---|---|
| 1,823,094 A | * | 9/1931 | Dylong .................. | 128/203.22 |
| 2,335,936 A | * | 12/1943 | Hanlon .................. | 128/203.22 |
| 2,672,138 A | * | 3/1954 | Carlock ................. | 128/203.22 |
| 3,905,335 A | | 9/1975 | Kapp | |
| 4,327,719 A | | 5/1982 | Childers | |
| 4,782,832 A | * | 11/1988 | Trimble et al. ......... | 128/207.18 |
| 5,417,205 A | * | 5/1995 | Wang ..................... | 128/206.11 |
| 5,485,836 A | | 1/1996 | Lincoln | |
| 5,568,808 A | | 10/1996 | Rimkus | |
| 5,665,104 A | | 9/1997 | Lee | |
| 5,775,335 A | | 7/1998 | Seal | |
| 6,012,455 A | | 1/2000 | Goldstein | |

FOREIGN PATENT DOCUMENTS

| | | | |
|---|---|---|---|
| WO | 87/05798 | * 10/1987 | .................. 128/848 |

* cited by examiner

Primary Examiner—Aaron J. Lewis
Assistant Examiner—Mital Patel
(74) Attorney, Agent, or Firm—Charles L. Thoeming

(57) ABSTRACT

The apparatus is configured to provide improved nasal breathing to persons requiring a range of respiratory based remedies ranging from opening collapsed nasal passages to treating allergic reaction to delivery of immediate dosage or controlled release medication. The apparatus includes connected nasal inserts which provide nodules to open the nasal passage and which directly align with the nasal air channel. For a preferred embodiment which provides a means to delivery of breathable gas mixtures or nasal and sinus rinse solutions, the inserts contain cannula which receive and connect to the source of the gas or rinse. For another embodiment using filtration, the inserts receive disposable filtration pacs. Sustained release of predetermined medical dosages is obtained by a further embodiment wherein the inserts receive medication inserts.

13 Claims, 10 Drawing Sheets

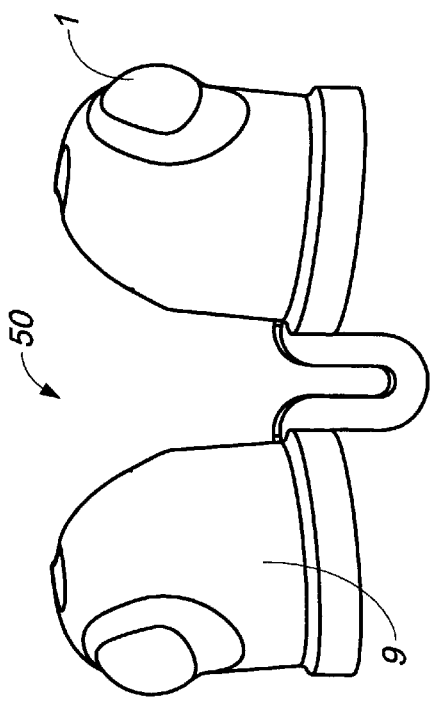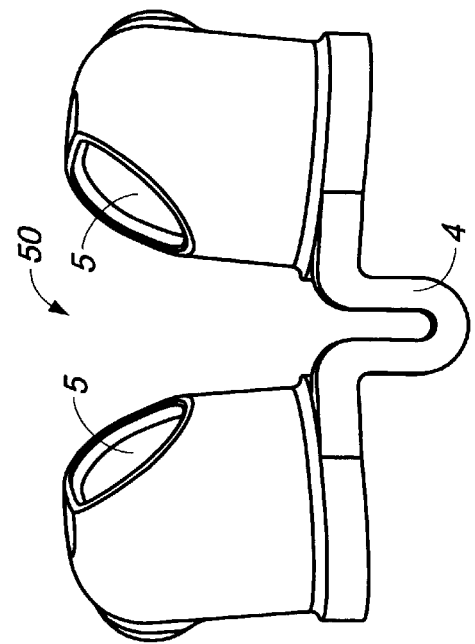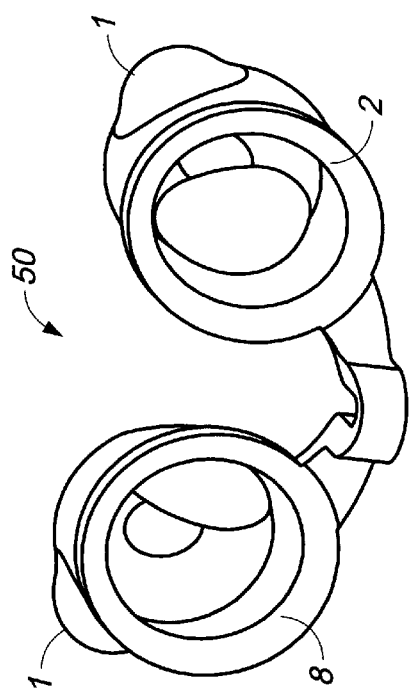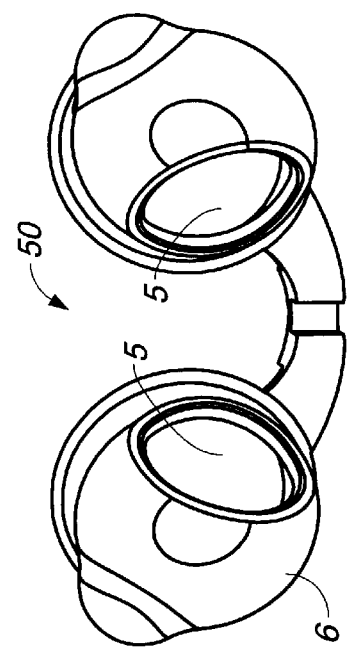
FIG._2A
FIG._2B
FIG._1A
FIG._1B

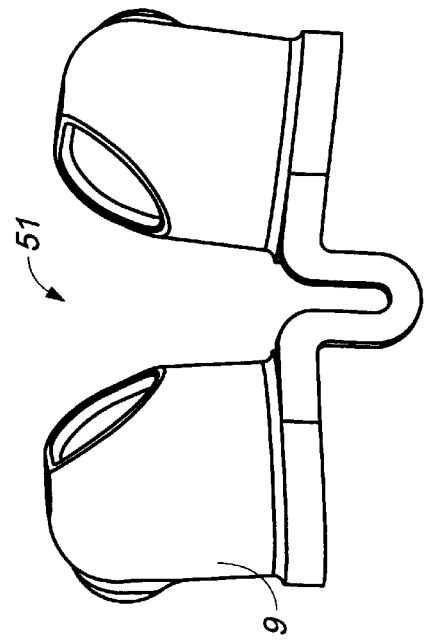
FIG._3B
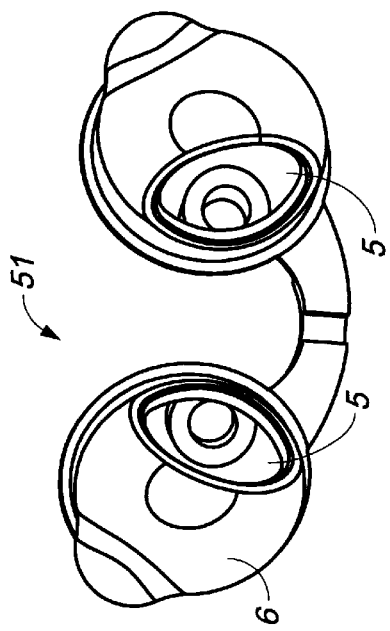
FIG._3D
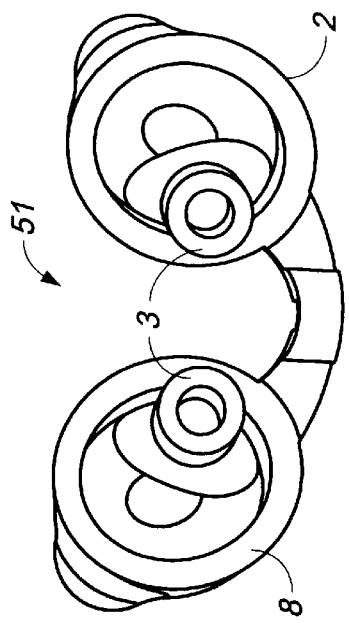
FIG._3A
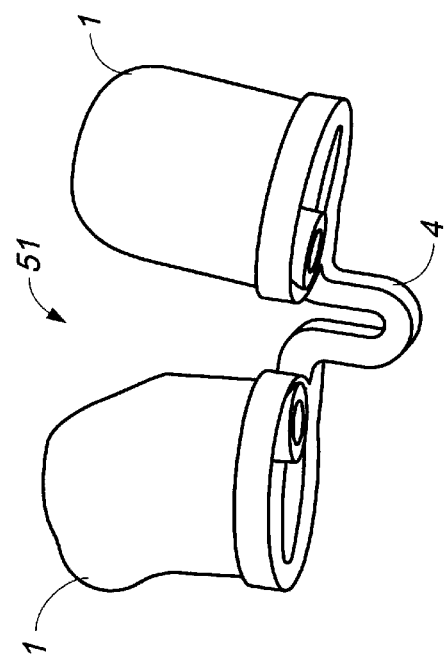
FIG._3C

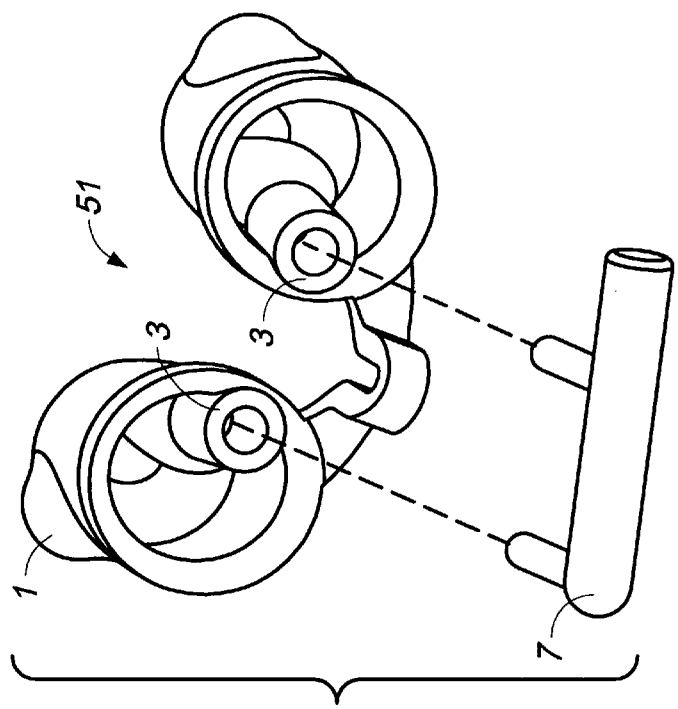
FIG._5
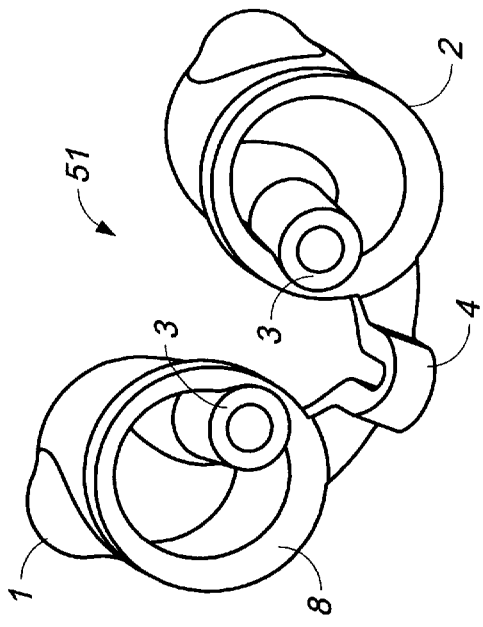
FIG._4A
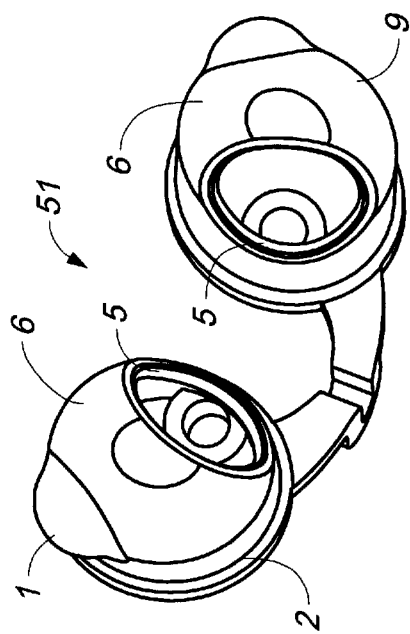
FIG._4B

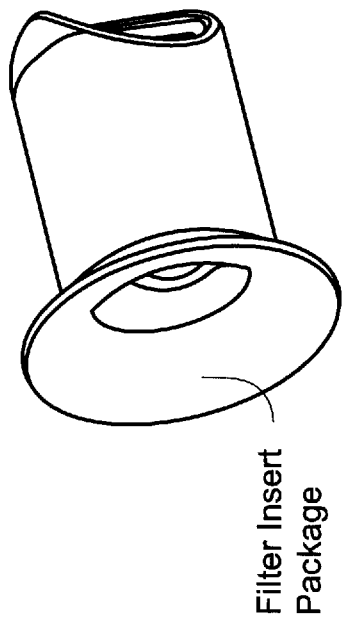
FIG._6B
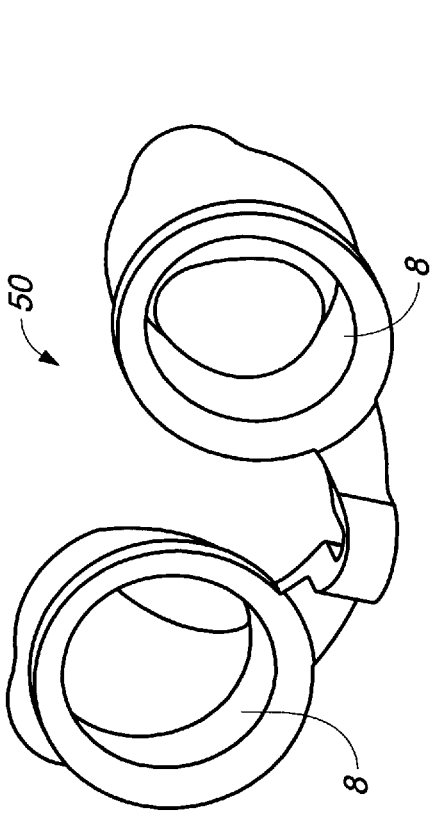
FIG._6A
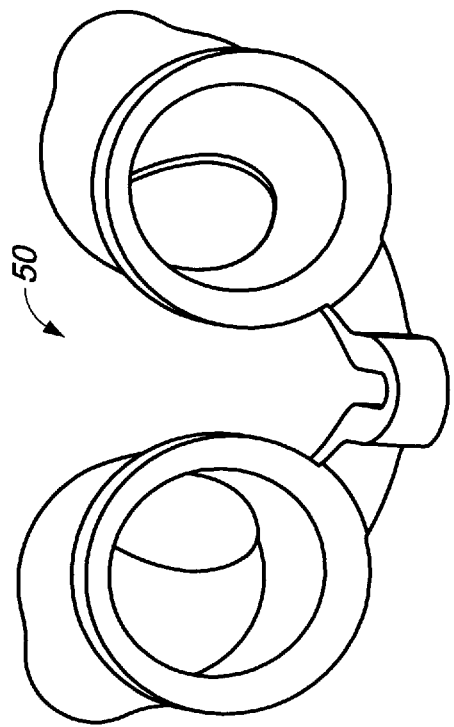
FIG._7B
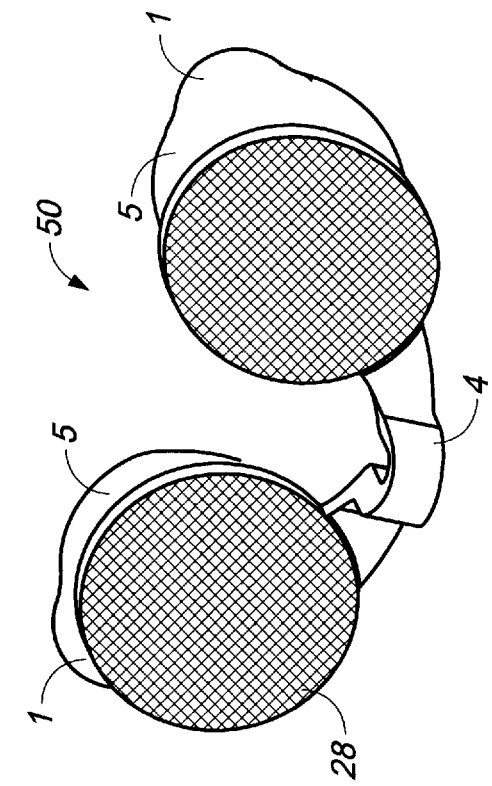
FIG._7A

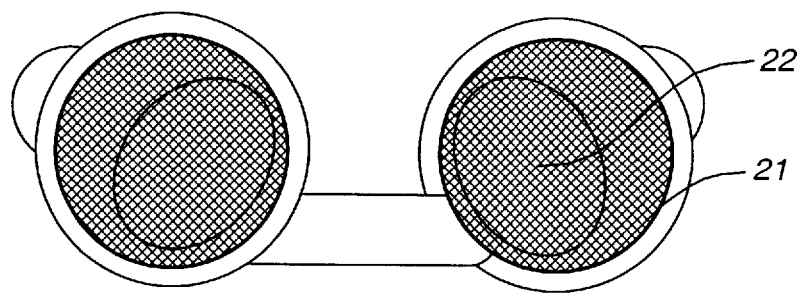
FIG._8A
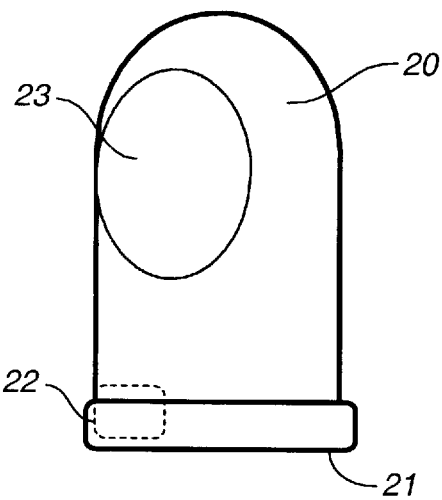
FIG._8B
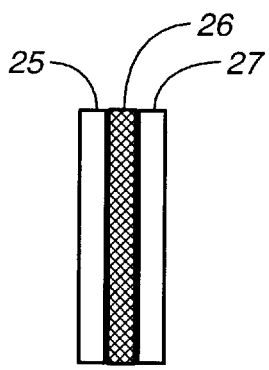 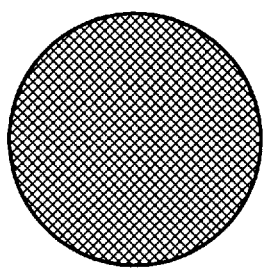 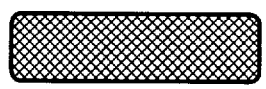
FIG._8C   FIG._8D   FIG._8E

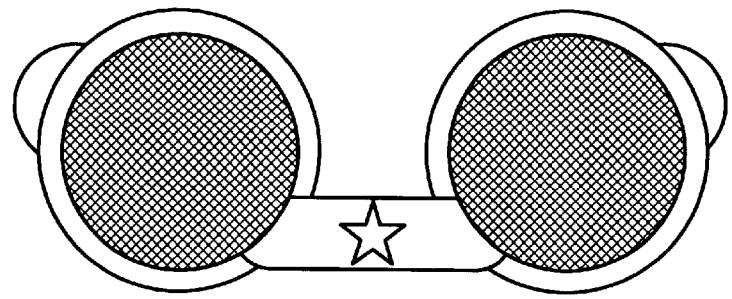
FIG._9A
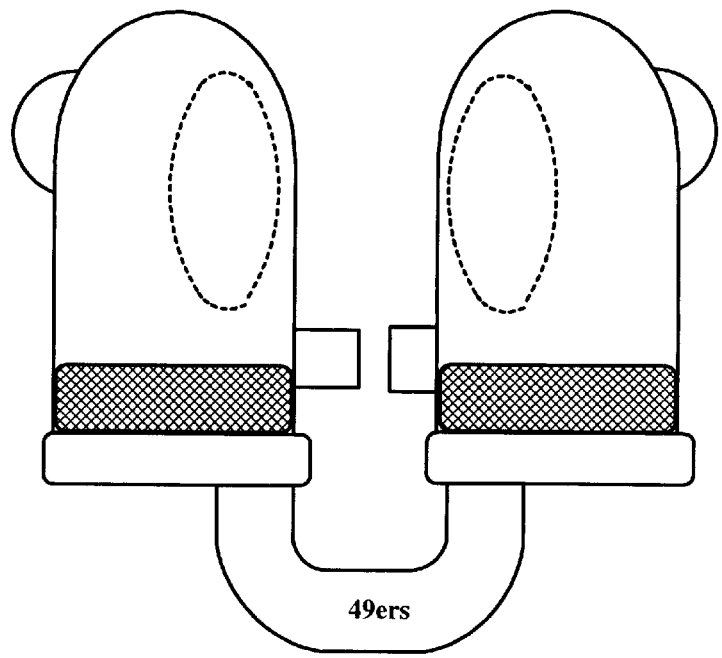
FIG._9B
FIG._9C
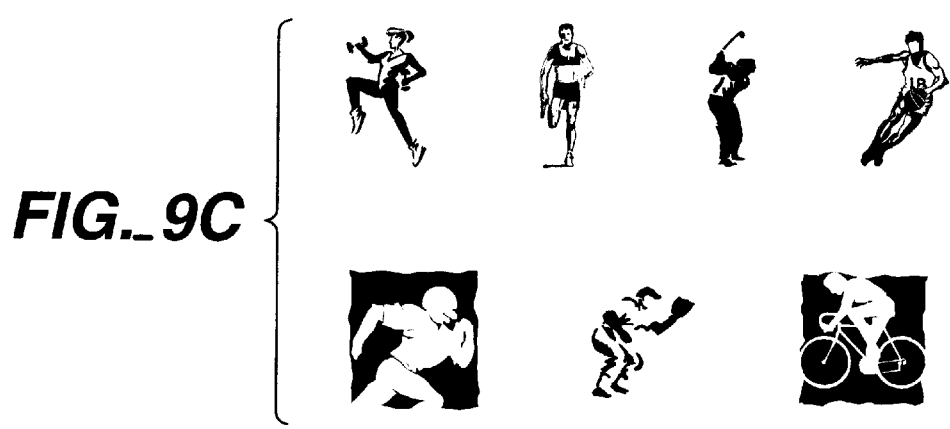

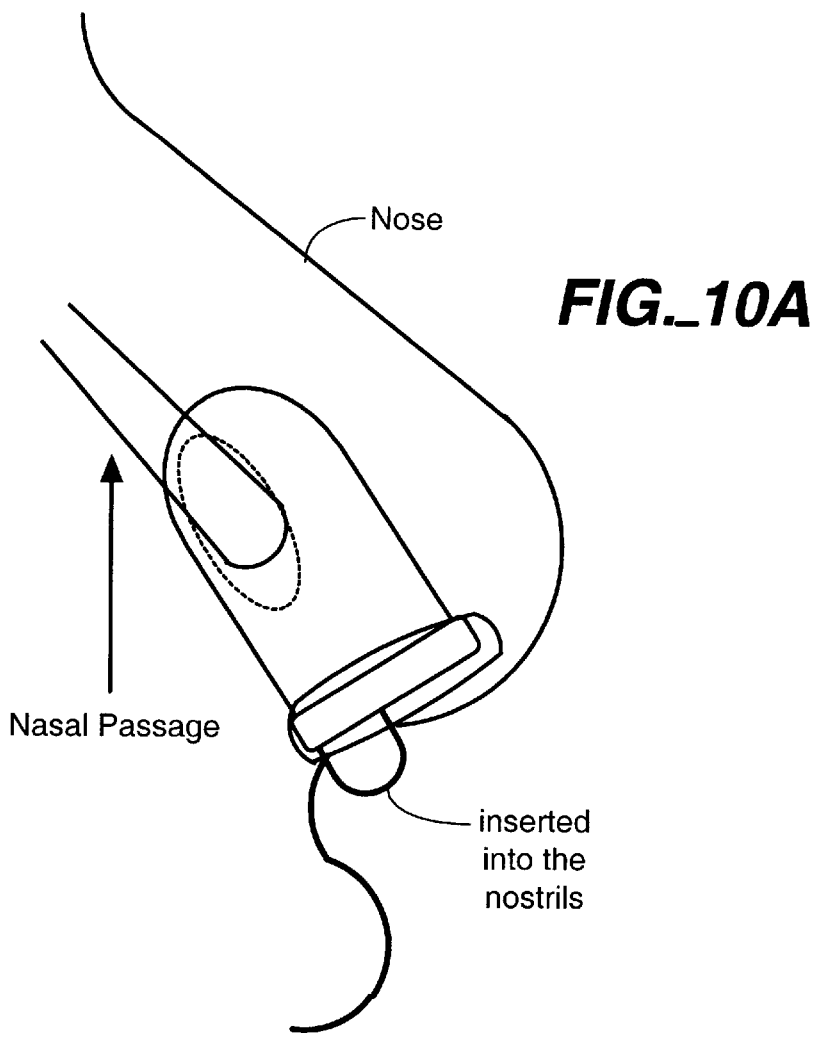
FIG._10A
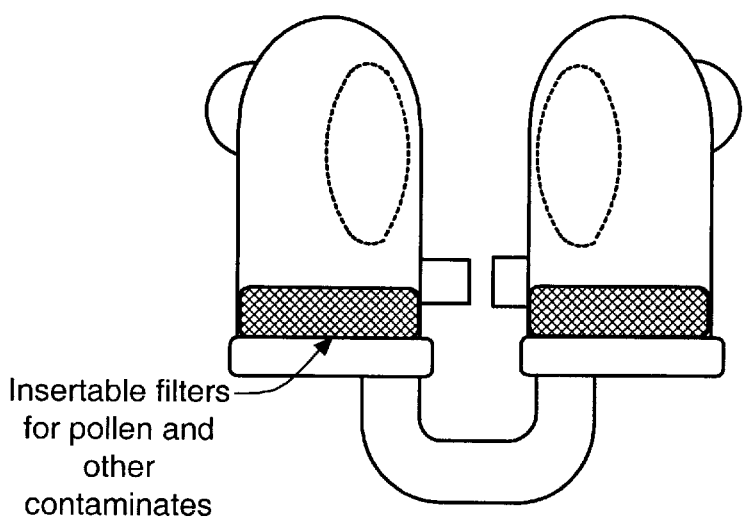
FIG._10B

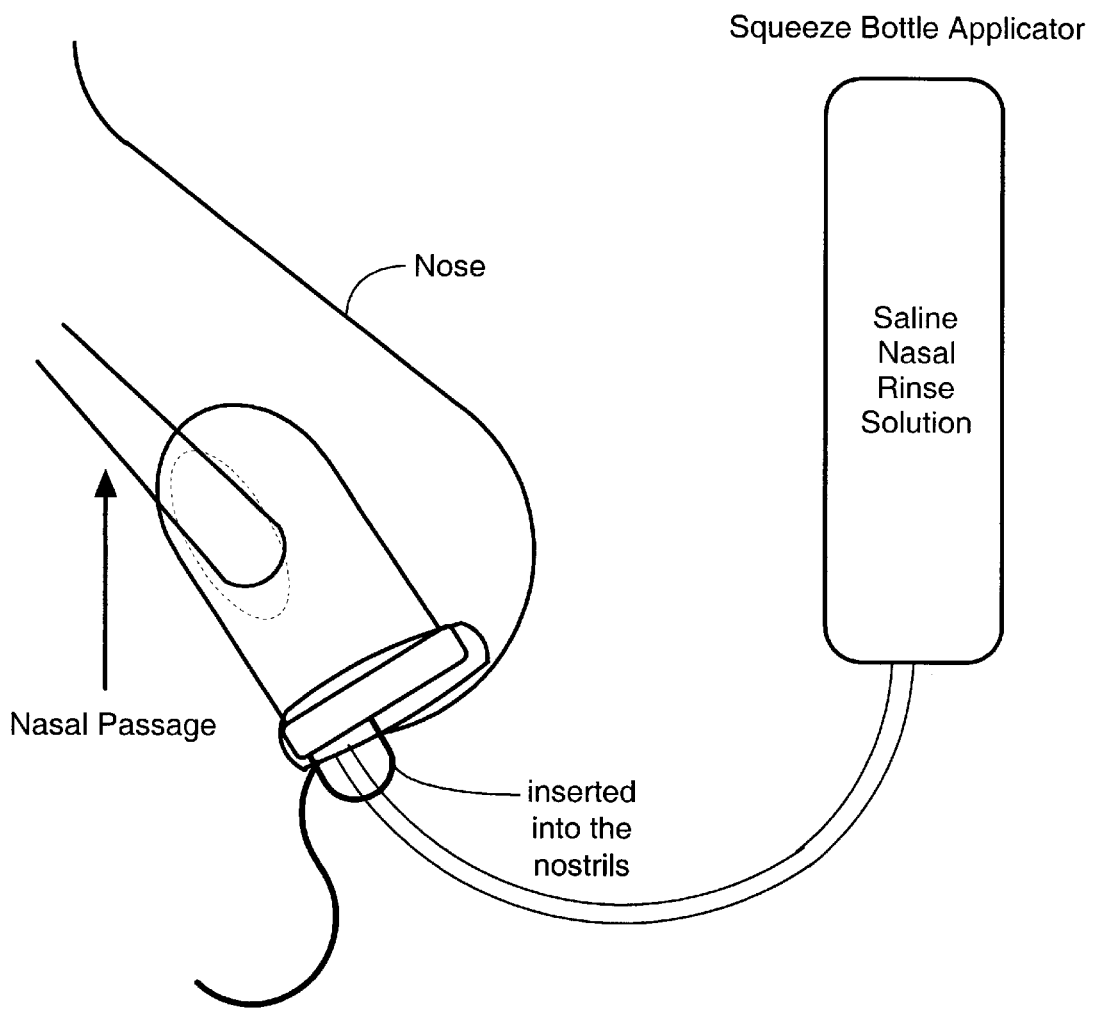
FIG._11

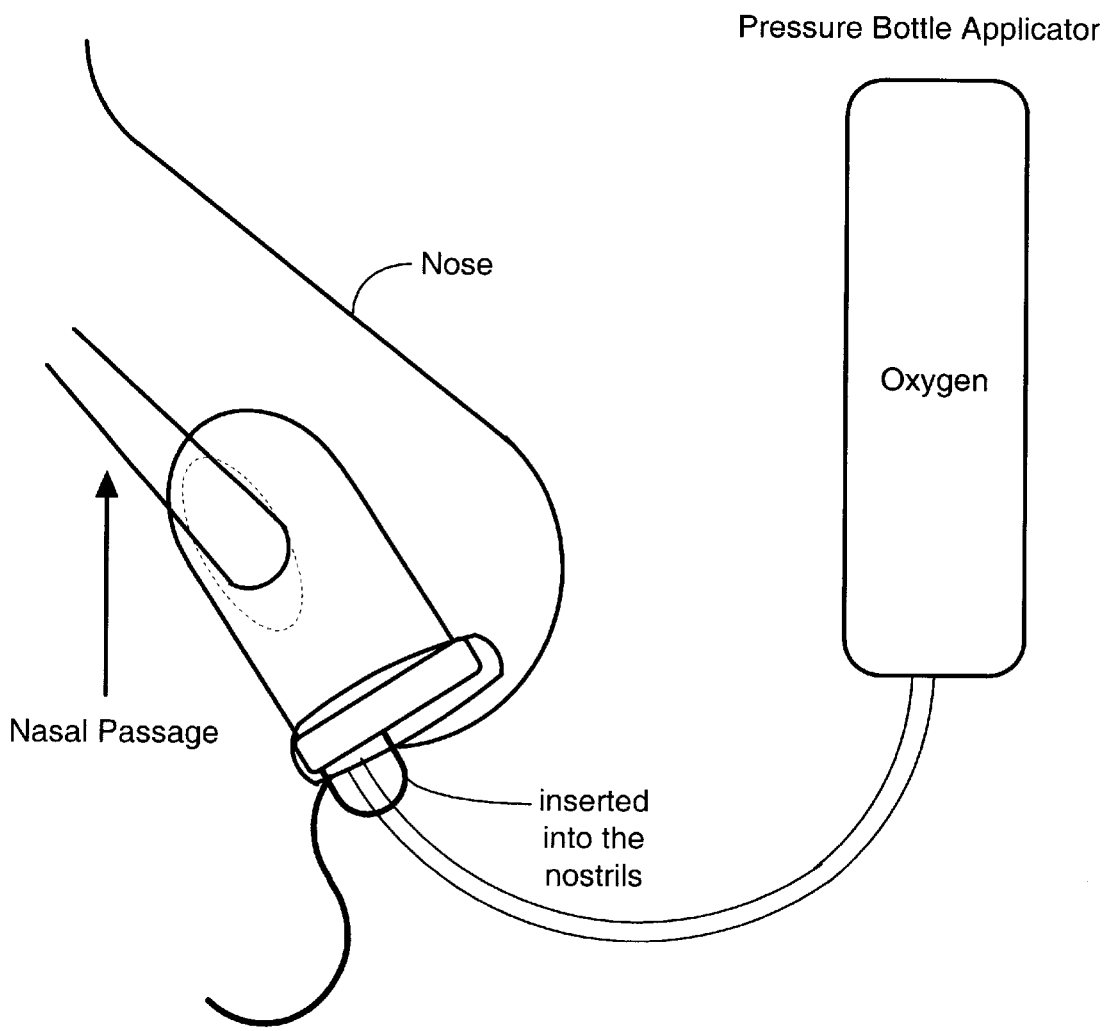
FIG._12

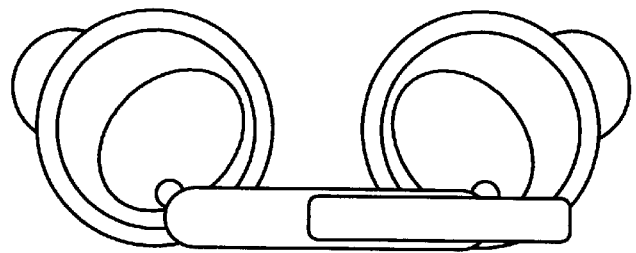
FIG._13A-1
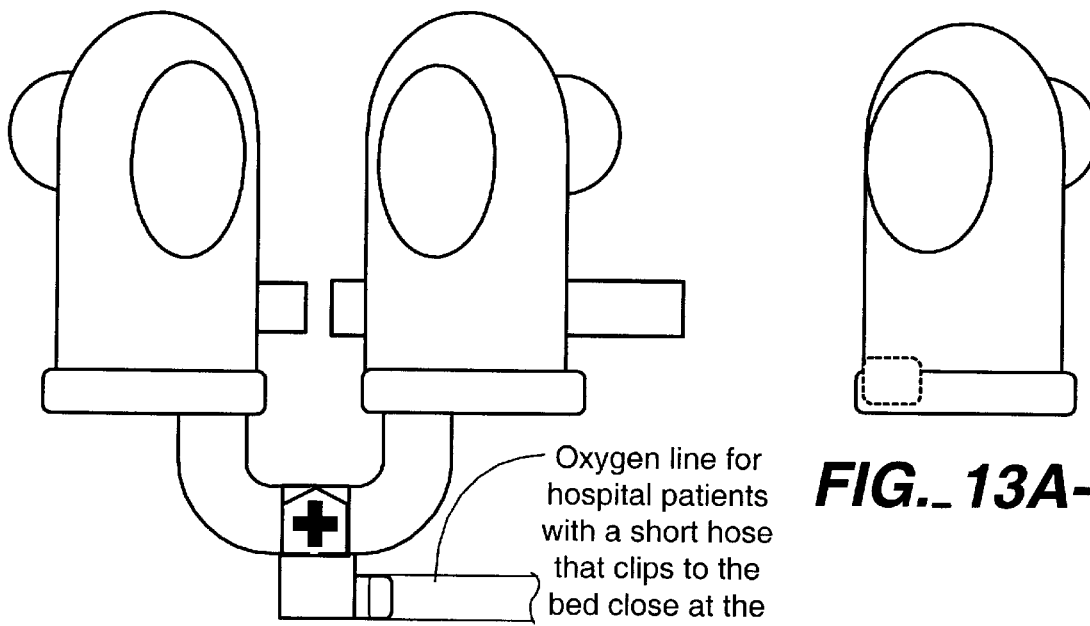
Oxygen line for hospital patients with a short hose that clips to the bed close at the shoulder collar
FIG._13A-2
FIG._13A-3
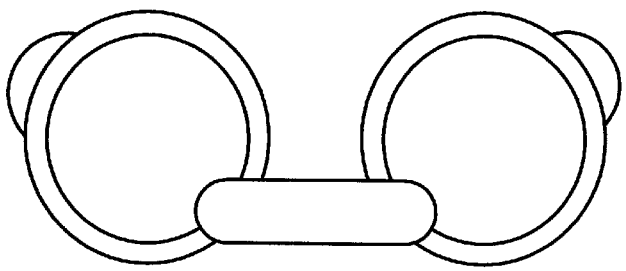
FIG._13B-1
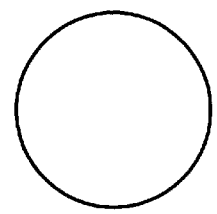
FIG._13B-2
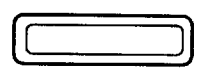
FIG._13B-3

NASAL BREATHING APPARATUS AND METHODS

A search of the prior art located the following United States patents which are believed to be representative of the present state of the prior art: U.S. Pat. No. 3,905,335, issued Sep. 16, 1975, U.S. Pat. No. 4,327,719, issued May 4, 1982, U.S. Pat. No. 5,485,836, issued Jan. 23, 1996, U.S. Pat. No. 5,568,808, issued Oct. 29, 1996, U.S. Pat. No. 5,665,104, issued Sep. 9, 1997, U.S. Pat. No. 5,775,335, issued Jul. 7, 1998, U.S. Pat. No. 6,012,455, issued Jan. 11, 2000. These references, however, suffer from one or more of the following disadvantages, as more specifically detailed below.

BACKGROUND

Flow of air outside the body to the lungs begins with the nose, which is divided into left and right nostrils. The nostrils perform two critical roles: they filter the air to remove potentially disease causing particles; and they moisten and warm the air to protect the respiratory system structures.

Each nostril further comprises three nasal passages to further divide inhaled air into three air flow streams; upper, median, and lower. Studies indicate inhaled air divides approximately into 9% to the upper nasal passage, 73% to the median nasal passage, and 18% to the lower nasal passage. Under normal function, this airflow distribution moistens and warms the inhaled air in the median and upper nasal passages, and opens the Para nasal sinuses. Upon normal nasal exhalation, these Para sinuses are washed by the exhaled airstream. Since the lower passage does not contain sinuses, the mucous membrane of the lower nasal passage carries the burden of cooling and desiccating inhaled air. Normal exhalation distribution reverses the inhalation ratios and divides approximately into 9% to the upper nasal passage, 18% to the median nasal passage, and 73% to the lower nasal passage. When both inhalation and exhalation function normally, the lower nasal passage exhalation exchange offsets the inhalation demands on the mucous membrane of the lower nasal passages.

When nasal passages do not function properly, untreated air enters the upper nasal passages and exerts a highly desiccating and cooling effect on the mucous membranes of the lower passages causing chronic inflammation. As this inflammation swells the lower passages, exhaled air is mostly directed to the median nasal passages, leaving the mucous membrane of the lower passages unprotected. This abnormal nasal breathing dynamic is conducive to frequent common colds, chronic rhinitis, vasomotor rhinitis, and associated sinus afflictions. Additionally, the pharynx in such abnormal breathing dynamics becomes dry and sub-atrophic, resulting in chronic pharyngitis. Left untreated, these conditions expand to the trachea and bronchi resulting in chronic tracheal bronchitis, asthmatic bronchitis, or other related ailments.

Optimal human breathing function also requires unrestricted nasal passages. Gravity, aging, eyeglass pressure, allergic reaction, among other causes, collapse human nasal passages and restrict airflow necessary for proper breathing function. Nasal passage irritation and swelling from increased levels of air pollution, particles, pathogens, and microorganisms entrained in ambient air contribute to reported higher levels of breathing problems, respiratory ailments, infection, and related pulmonary disease. The impact of these infirmities increases in highly populated metropolitan areas. These infirmities are compounded in third-world countries by the lack of an economic, disposable means to address the underlying problem of nasal airway obstruction and to serve as a platform to guard against pollutants inhaled into the respiratory system or to medicate or otherwise treat the biological reaction(s) thereto.

Many existing nasal filters impose mechanical filters in nasal passages making breathing unnatural and increasingly difficult. These filters do not resemble the manner in which the nose works to filter inhaled air. The nose filters air by getting the air to travel in a curved pathway in which the air flows around and while air entrained particles go straight ahead and impact on the nasal lining or nasal hairs.

Existing nasal filters also are not discreet, are not ergonomically fitted to the nostril, and are uncomfortable to wear for more than brief periods at a time. Most irritate the interior nasal tissue without addressing a principal cause of restricted nasal passages, sagging nasal tissues in the bridge area of the nose. Exterior strips have been successful in certain sports applications or for addressing sleep apnea or snoring; however, these devices lack the ability to filter inhaled air, or otherwise to provide a platform for additional rhinal based medications, therapies, or treatments.

Present nasal filters and inserts do not provide any known means for sampling the environmental allergens or pollutants an individual wearer is exposed to for a given application or time period. Thus, the present art cannot serve as a means for counter-acting those same irritant sources by a prescribed release medication or filtration system. Although medicated therapies for asthma and hay fever have improved massively in recent years, delivery of timed release potions of these medications prescribed to the patient's particular needs is limited to externally applied inhalers, ingested oral medications, or inoculation. A rhinal, time release platform for administering these advances in medication is a necessary and cost effective alternative to the present applications. This advancement is particularly attractive to persons concerned about over medication, medication dosage levels, or possible negative synergistic side effects of orally ingested medication.

For the foregoing reasons, there is a need for an inexpensive, disposable nasal breathing apparatus for use in overcoming sleep apnea, improving athletic performance, filtering or otherwise treating inhaled air, or as a platform for various medical applications.

SUMMARY

This invention relates generally as indicated to an inexpensive, sterile, disposable nasal breathing apparatus for use in overcoming sleep apnea, filtering or otherwise treating inhaled air, a platform for delivering medication, or improving athletic performance.

A principal object of the present invention is to lift the nasal wall away from the internal nasal passage opening, thus reducing obstruction in breathing through the nose sometimes caused by gravity, the aging process, allergic reactions, or external pressure from reading glasses. The unique shape of the nasal insert allows for optimal air passage while affording comfort to the wearer. Another object of the preferred embodiment of this invention is to provide an inexpensive, disposable apparatus to increase the volume of airflow through the nasal passages for persons participating in sporting events or other activities which increase functional demands upon the cardiovascular and respiratory systems.

Another object of the present invention is to provide an inexpensive and disposable platform from which air inhaled through the nostrils is filtered or otherwise treated.

Another object of the present invention is to provide an inexpensive and disposable platform to deliver a predetermined dosage of prescribed medication. Use of a bio-adhesive or similar membrane inserts as part of the nasal apparatus allows inhalation of atomized medication into the nasal mucosa and absorption into the bloodstream. Use of such bio-adhesive or similar membrane inserts would provide the wearer medical applications including without limitation for aroma therapy, immunization, psychological treatment, geriatric medications, pain control or relief, or chemotherapy.

Another object of the present invention is to provide an improved method for the ventilation of oxygen or other gaseous elements, medications or anesthetics into the nasal passage without unduly drying or irritating the interior nasal tissue.

Another object of the present invention is to provide an inexpensive, disposable apparatus to support a personally customized sinus rinse system wherein the wearer can flush the sinus cavities with a mild saline solution, or similarly functioning mixture, to flush bacteria, debris, or mucosa congestion from the sinus cavities.

These together with other objects of the invention, along with the various features of novelty which characterize the invention, are described with particularity in the claims attached to and forming a part of this disclosure. For a better understanding of the invention, its operating advantages and the specific objects attained by its uses, reference should be made to the attached drawings and descriptive materials in which there are illustrated preferred embodiments of the invention. Other features, advantages, and objects of the present invention will become apparent with reference to the following description and accompanying drawings.

BRIEF DESCRIPTION OF DRAWINGS

These and other features, aspects, and advantages of the present invention will become better understood with regard to the following description, appended claims, and accompanying drawings where:

FIG. 1A presents a front view of the first embodiment of the present invention; and FIG. 1B presents a rear view of the first embodiment of the present invention; and FIG. 2A presents a top view of the first embodiment of the present invention; and FIG. 2B presents a bottom view of the first embodiment of the present invention; and FIG. 3A presents a front view of the second embodiment of the present invention; and FIG. 3B presents a rear view of the second embodiment of the present invention; and FIG. 3C presents a top view of the second embodiment of the present invention; and FIG. 3D presents a bottom view of the second embodiment of the present invention; and FIG. 4A is an isometric view of the front of the second embodiment of the present invention; and FIG. 4B is an isometric view of the back of the second embodiment of the present invention; and FIG. 5 is an isometric front angle view of the second embodiment of the present invention with cannula inserts in position for placement into the cannula; and FIG. 6A is an isometric front angle view of the first embodiment of the present invention ready to receive a filter insert package into the open annular end; and FIG. 6B is an isometric view of a filter insert package for placement into the open annular end of the first embodiment of the present invention shown in FIG. 6A; and FIG. 7A is an isometric view of the first embodiment of the present invention with filter disks inserted into the open annular ends; and FIG. 7B is an isometric view of the first embodiment of the present invention with filter disks removed from the open annular ends; and FIG. 8A is a front view of medical filter plug inserts inserted into the open annular ends of the first embodiment of the present invention; and FIG. 8B is a bottom view of one of the cylindrical inserts of the first embodiment of the present invention with a medical filter inserted into the open annular end; and FIG. 8C is a side view of a representative medical filter plug insert suitable to be inserted into the open annular ends of the first embodiment of the present invention; and FIG. 8D is a front view of a representative medical filter plug insert suitable to be inserted into the open annular ends of the first embodiment of the present invention; and FIG. 8E is a top view of a representative medical filter insert suitable to be inserted into the open annular ends of the first embodiment of the present invention; and FIG. 9A is a front view of various allergy relief medical inserts for the first embodiment of the present invention with a team logo on the elongated flex joining the cylindrical inserts; and FIG. 9B is a top view of various allergy releif medical inserts for the first embodiment of the present invention with a team logo on the elongated flex joining the cylindrical inserts; and FIG. 9C are representative samples of suitable sports action figures for display on the elongated flex joining the cylindrical inserts of the first embodiment of the present invention; and FIG. 10A is a view of the first embodiment of the present invention placed into the nasal passage using insertable filter plugs for pollen and other contaminates; and FIG. 10B is a bottom view of the first embodiment of the present invention with insertable filter plugs for pollen and other contaiminates fitted into the open annular ends; and FIG. 11 is a view of the second embodiment of the present invention inserted into the nostril and fitted with a means to rinse the sinuses; and FIG. 12 is a view of the second embodiment of the present invention inserted into the nostril and fitted with a means to deliver oxygen to the nasel passage; and FIG. 13A-1 is an open end, front view of the second embodiment of the present invention with oxygen inlets fitted into the cannula to deliver oxygen to the respiratory system through the nasal passages;

FIG. 13A-2 is a bottom view of the second embodiment of the present invention with oxygen inlets fitted into the cannula to deliver oxygen to the respiratory system through the nasal passages; and FIG. 13A-3 is a side view of one of the cylindrical inserts of the first embodiment of the present invention with a medication strip insert fitted into the open annular end; and FIG. 13B-1 provides an open end, front view of the first embodiment of the present invention with medication inserts fitted into the open end to deliver slow release medication to the patient's nasal passages for absorption through the sinuses; and FIG. 13B-2 provides a front view of a medication insert suitable to be fitted into the open end of the first embodiment of the present invention to deliver slow release medication to the patient's nasal passages for absorption through the sinuses; and FIG. 13B-3 provides a to view of a medication strip insert suitable to be fitted into the open end of the first embodiment of the present invention to deliver slow release medication to the patient's nasal passages for absorption through the sinuses.

DESCRIPTION

The detailed description, as set forth below, in connection with the appended drawings is intended as a description of the construction and operation of the preferred embodiment of the invention, and is not intended to represent the only form in which the present invention may be constructed or operated. It is to be understood that the invention may be practiced by other different embodiments, which are also encompassed within the spirit and scope of the invention.

The first preferred embodiment of the nasal breathing apparatus 50 of this invention is generally indicated in FIGS. 1A, 1B, 2A and 2B. The apparatus comprises dual cylindrical nasal inserts 9 each of which has a dome end 6, a open annular flanged end 2 which forms a seal with the lower external portion of the nostril, and a cavity 8 located between the dome end 6 and the open annular flanged end 2. The anterior exterior of each domed end 6 has a rigid nodule 1 affixed thereto to engage and lift nasal tissue away from the natural nasal air channel. The posterior of each domed end 6 has an elliptical opening 5 aligned with the natural nasal air channel. The dual cylindrical nasal inserts 9 are connected by a rigid elongated flex 4 attached to the posterior exterior of each open annular flanged end 2. This elongated flex connection of the nasal inserts serves to assist the wearer to insert, position, seal, secure, or remove the nasal inserts, as well as to provide a platform for additional embodiments of the present invention as developed further in this description below. The dual cylindrical nasal inserts 9, the elongated flex 4, the dome end 6, the open annular flanged end 2, and the rigid nodule 1 are preferably made of a fairly stiff but flexible synthetic polymer composition material. This material is preferably sufficiently soft so that it can properly seal around the nostril opening on persons of different facial configurations. The dual cylindrical nasal inserts 9, the rigid elongated flex 4, the dome end 6, the open annular flanged end 2, and the rigid nodule 1 are injection molded in three (3) sizes from a medical grade, non-allergenic silica rubber. As a further embodiment of the present invention, medication inserts can be placed on inside of open annular flanged end 2 as depicted in FIGS. 13A-3, 13B-1, 13B-2, and 13B-3. These medication inserts can be readily disposed of and replaced according to prescribed dosages of timed or other controlled release medications which can be administered to a patient fitted with this embodiment of the present invention. In this manner, numerous symptom control medications can be administered for immediate treatment for pain, diabetes, migraine headaches, irregular coronary symptoms, among other suitable applications.

A second preferred embodiment of the nasal breathing device of this invention 51 is shown in FIGS. 3A, 3B, 3C, 3D, 4A, 4B, and 5. In this embodiment, each nasal insert houses a semi-rigid polymeric cannula 3 affixed to the posterior interior of the cavity 8 and directionally aligned with the open annular flanged end 2 and the elliptical opening 5. In this embodiment the cannula 3 receive delivery inserts 7 of FIG. 5 as a means for delivery of breathable gaseous mixtures or nasal rinse solutions to the cylindrical nasal inserts 9.

In a further embodiment of this present invention FIG. 5, the delivery inserts 7 are affixed to the cannula 3 and serve as the means to deliver rinsing solution, FIG. 11, or gaseous mixtures such as oxygen, FIG. 12, to the nasal passages.

As shown in FIGS. 6A and 6B a further embodiment of this present invention 50 a cylindrical plug insert, FIGS. 8B, 8C, and 8D, comprising a dome end 20, an open annular end 21, a cavity 22 located between the dome end 20 and open annular end 21, and an elliptical opening in the posterior of the dome end 23, is inserted into the open annular flanged end 2 of the cylindrical nasal inserts 9 and affixed thereto at the open annular flanged end 2. This elliptical opening in the posterior of the dome end 23 of this cylindrical plug insert is aligned with the elliptical opening 5 of the posterior of the nasal insert dome of FIG. 6A. This cylindrical plug insert comprises three layers: an external micron fiber filter layer 25, a middle charcoal filter layer 26, and an internal slow release anti-histamine layer 27, as further depicted in FIG. 8C.

In a further embodiment of this present invention 50 the cylindrical plug insert shown in FIG. 6B has an end cap 28 shown in FIGS. 8A, 9A, 10A and 10B affixed to the open annular end 21 as further shown in FIG. 7A. The end cap has at least one air passageway and comprises a synthetic fiber disc membrane bonded to a dissolvable layer containing chitosan. These cylindrical plug insert caps can be disposable filters serving to eliminate a variety of airborne contaminates such as pollen, soot, ash particulate, and the like.

In a further embodiment of this present invention 50 or 51 the rigid elongated flex 4 of FIGS. 2B or 4A provides a platform for displaying embossed logos as depicted in FIGS. 9A or 9B for attaching jewelry or gems.

In operation, apparatus 51 is utilized as delivery means for a method to rinse the sinuses as depicted in FIG. 11. As shown, the user inserts the apparatus 51 into the nostrils. The apparatus 51 is then connected to a source of nasal rinse solution which enters the apparatus through cannula inserts FIG. 7 fitted into the cannula of the apparatus 51. The delivery means for supplying the nasal rinse solution is engaged and adjusted to allow the desired level of rinse solution flow. The rinse solution is inhaled into the sinuses and expectorated through the mouth of the user.

In operation, apparatus 51 is utilized as delivery means for a method to deliver gaseous mixtures to the respiratory system as depicted in FIGS. 12, 13A-1, and 13A-2. As shown, the user inserts the apparatus 51 into the nostrils. The apparatus 51 is then connected to a source of gaseous mixture under regulated pressure. The gaseous mixture enters the apparatus through cannula inserts 7 fitted into the cannula of the apparatus 51 as depicted in FIG. 5. The delivery means for supplying the gaseous mixture is engaged and adjusted to allow the desired level of gaseous mixture flow. The gaseous mixture is inhaled into the nasal passages and to the user's lungs, and exhaled through the mouth of the user.

While in the foregoing, embodiments of the present invention have been set forth in considerable detail for the purpose of making a complete disclosure of the invention, it may be apparent to those of skill in the art that numerous changes may be made in such detail without departing from the spirit and principles of the invention This invention has been described in its presently contemplated best modes and embodiments and it is clear that it is susceptible to numerous modification, modes and embodiments within the ability of those skilled in the art and without the exercise of the inventive faculty. Accordingly, the scope of this invention is defined by the scope of the following claims. Therefore, the foregoing is considered as illustrative only of the principles of the invention.

Additionally, since numerous modifications and changes will readily occur to those skilled in the art, it is not desired to limit the invention to the exact construction and operation shown and described, and further, all suitable modifications and equivalents may be resorted to, falling within the scope of the invention.

I claim:

1. An improved nasal breathing device comprising:
   a nasal insert which serves to open collapsed nasal breathing passages while replicating the utilitarian function of the natural nasal air channel of the nostril and which further comprises:
      semi-rigid polymeric dual cylindrical nasal inserts each comprising a dome end having an anterior end, a posterior end, an exterior surface, and an interior surface, and an open annular flanged end having an anterior end, a posterior end, an exterior surface, and an interior surface, and which open annular flanged end is adapted to form a seal with the lower external portion of the nostril, and a cavity located between the dome end and the open annular flanged end;
   a rigid polymeric nodule affixed to the anterior exterior of each nasal insert dome end, and which is adapted to engage the nasal tissue to lift the tissue away from the natural nasal air channel;
   an elliptical opening in the posterior of each nasal insert dome end aligned with the natural nasal air channel;
   a rigid polymeric cannula having two ends longitudinally affixed to the posterior interior of each nasal insert open annular flanged end with one cannula end aligned with the open annular flanged end and the other cannula end aligned with the elliptical opening; and
   a rigid elongated flex affixed to the posterior exterior of each nasal insert open annular flanged end, the rigid elongated flex serving to insert, position, seal, align and secure the nasal inserts within the nostrils and to remove the inserts from the nostrils.

2. The nasal breathing device of claim 1 further comprising means for delivering breathable gas mixtures to the nose through the rigid polymeric cannula.

3. The nasal breathing device of claim 1 further comprising means for delivering a nasal rinse solution to the nose through the rigid polymeric cannula.

4. An improved nasal breathing device comprising:
   a nasal insert which serves to open collapsed nasal breathing passages while replicating the utilitarian function of the natural nasal air channel of the nostril and which further comprises:
      semi-rigid polymeric dual cylindrical nasal inserts each comprising a dome end having an anterior end, a posterior end, an exterior surface, and an interior surface, and an open annular flanged end having an anterior end, a posterior end, an exterior surface, and an interior surface, and which open annular flanged end is adapted to form a seal with the lower external portion of the nostril, and a cavity located between the dome end and the open annular flanged end;
   a rigid polymeric nodule affixed to the anterior exterior of each nasal insert dome end, and which is adapted to engage the nasal tissue to lift the tissue away from the natural nasal air channel;
   an elliptical opening in the posterior of each nasal insert dome end aligned with the natural nasal air channel;
   internally fitted means disposed within the nasal insert to filter nasally inhaled air; and
   a rigid elongated flex affixed to the posterior exterior of each nasal insert open annular flanged end, the rigid elongated flex serving to insert, position, seal, align and secure the nasal inserts within the nostrils and to remove the inserts from the nostrils.

5. The nasal breathing device of claim 4 wherein the internally fitted means disposed within the nasal insert to filter nasally inhaled air further comprises:
   a cylindrical plug insert having an external micron fiber layer, a middle charcoal filter layer, and an internal timed release anti-histamine layer, an anterior end, a posterior end, a plug dome end and a plug open annular end, and a cavity located between the plug dome end and the plug open annular end;
   an elliptical opening in the posterior of the plug nasal insert plug dome end aligned with the elliptical opening in the posterior end of the nasal insert dome; and
   means for interconnecting the plug assembly to the nasal insert open annular, flanged end.

6. The nasal breathing device of claim 4 wherein each nasal insert to filter nasally inhaled air further comprises internally fitted means disposed within the cylindrical nasal insert to deliver medication.

7. The nasal breathing device of claim 6 wherein the internally fitted means disposed within the cylindrical nasal insert to deliver medication further comprises a synthetic fiber disc membrane bonded to a dissolvable layer containing chitosan.

8. The nasal breathing device of claim 6 wherein the internally fitted means disposed within the nasal insert to deliver medication further comprises a cap comprising a center and containing a plurality of holes concentrically located around the center of the cap in three varying radiuses providing concentric rings of holes, each hole in the center concentric ring of the holes being twice the diameter of each hole of the inner radius and half the diameter of each hole of the outer radius, the cap communicating with and connectedly disposed within the open annular end.

9. The nasal breathing device according to either of claims 1 or 4 wherein the rigid elongated flex further comprises means for displaying embossed logos.

10. The nasal breathing device according to either of claims 1 or 4 wherein the rigid elongated flex further comprises means for attaching jewelry.

11. The nasal breathing device according to either of claims 1 or 4 wherein the rigid elongated flex further comprises means for attaching gems.

12. A method for inhaling a breathable mixture of gas according to a prescribed application comprising:
   inserting the nasal breathing apparatus of claim 2 into the nostrils;
   affixing the nasal breathing apparatus to means for supplying breathable air;
   turning on the means for supplying breathable air;
   adjusting the air flow on the means for supplying breathable air to suit the prescribed application;
   inhaling the air flow from the means for supplying breathable air through the nostrils; and
   exhaling through the mouth.

13. A method for rinsing the sinus cavities according to a prescribed application comprising:
   inserting the nasal breathing apparatus of claim 3 into the nostrils;
   affixing the nasal breathing apparatus to means for supplying a nasal rinse solution;
   turning on the means for supplying a nasal rinse solution;
   adjusting the flow on the means for supplying a nasal rinse solution to suit the prescribed application;
   inhaling the rinse solution into the sinuses from the means for supplying a nasal rinse solution through the nostrils; and
   expectorating the rinse solution through the mouth.

* * * * *